United States Patent
Kanashima et al.

(10) Patent No.: US 6,893,831 B1
(45) Date of Patent: May 17, 2005

(54) IMMUNOASSAY OF PIVKA-II

(75) Inventors: Motohito Kanashima, Toride (JP); Tomohide Asai, Ushiku (JP); Hiroki Takahashi, Ikoma (JP); Yoshiyuki Asai, Yono (JP)

(73) Assignee: Sanko Junyaku Co., Ltd., Tokyo (JP)

( * ) Notice: Subject to any disclaimer, the term of this patent is extended or adjusted under 35 U.S.C. 154(b) by 450 days.

(21) Appl. No.: 09/869,917

(22) PCT Filed: Jun. 1, 2000

(86) PCT No.: PCT/JP00/03550

§ 371 (c)(1),
(2), (4) Date: Jul. 9, 2001

(87) PCT Pub. No.: WO01/44810

PCT Pub. Date: Jun. 21, 2001

(30) Foreign Application Priority Data

Dec. 14, 1999 (JP) .......................................... 11-354862

(51) Int. Cl.⁷ .......................... C07K 16/36; C12N 5/20; C12Q 1/56; G01N 33/543; G01N 33/573
(52) U.S. Cl. ...................... 435/7.94; 435/7.23; 435/7.4; 435/7.6; 435/7.92; 435/13; 435/452; 435/337; 435/338; 435/962; 436/518; 436/534; 436/548; 530/384; 530/388.25; 530/388.26; 530/389.3
(58) Field of Search .................. 435/7.1, 7.23, 435/7.4, 7.6, 7.92, 7.94, 13, 452, 337, 338, 344.1, 962; 436/518, 534, 548; 530/382, 384, 388.25, 388.26, 389.3

(56) References Cited

U.S. PATENT DOCUMENTS 4,780,410 A * 10/1988 Matsuda et al. .............. 435/13
5,516,640 A * 5/1996 Watanabe et al. ............ 435/7.4

FOREIGN PATENT DOCUMENTS

| JP | 5-249108 | 9/1993 |
| JP | 5-284994 | 11/1993 |
| JP | 7-313186 | 12/1995 |
| JP | 9-43237 | 2/1997 |
| JP | 9-249699 | 9/1997 |

OTHER PUBLICATIONS

Lämmle et al., 1985. "Formation of the fibrin clot: the balance of procoagulant and inhibitory factors," in *Clinics In Haematology. Coagulation Disorders.* (Ruggeri, ed.) W.B. Saunders Company, London. pp. 281–285.*

Weir, 1978. *Handbook of Experimental Immunology.* Blackwell Scientific Publications, Oxford. p. 12. 13.*

* cited by examiner

*Primary Examiner*—Christopher L. Chin
*Assistant Examiner*—James L. Grun
(74) *Attorney, Agent, or Firm*—Wenderoth, Lind & Ponack, L.L.P.

(57) ABSTRACT

The present invention provides an immunoassay for specifically measuring with high sensitivity PIVKA-II in serum or plasma through antigen-antibody reaction by adding an animal serum containing thrombin and/or an antibody reacting with human fibrin-like related substances to the reagents. The immunoassay of the invention comprises the steps of adding thrombin and/or an antibody reacting with human fibrin-like related substances to the reagents, and measuring PIVKA-II in serum or plasma.

3 Claims, No Drawings

IMMUNOASSAY OF PIVKA-II

This application is a 371 of PCT/JP00/03550 filed Jun. 1, 2000.

TECHNICAL FIELD

The present invention relates to an immunoassay utilizing an antigen-antibody reaction for specifically measuring with high sensitivity PIVKA-II (Protein Induced by Vitamin K Absence or Antagonist-II) in serum or plasma by adding thrombin and/or an antibody reacting with human fibrin-like related substances to the reagents.

BACKGROUND ART

Along with AFP (α-fetoprotein), PIVKA-II (Protein Induced by Vitamin K Absence or Antagonist-II) is measured widely in clinical examination laboratories as a hepatic cell tumor detecting marker which specifically increases in hepatic cell cancer patients. Generally, magnetic beads, glass beads, plastic plates, latexes or the like on which PIVKA-II specific monoclonal or polyclonal antibodies are adsorbed are subjected to a first reaction with serum or plasma. Then, after washing the reaction mixture for B/F separation, a second reaction is carried out by adding human prothrombin specific polyclonal or monoclonal antibodies labeled with an enzyme, a fluorescent material, a radioisotope, an Ru complex or the like. Then, after washing the reaction mixture for B/F separation, the absorbance or luminescence of the enzyme, the fluorescent material, the radioisotope or the Ru bound to an immune complex formed by the antigen-antibody reaction is measured to determine PIVKA-II in the serum or the plasma.

Heretofore, PIVKA-II has been measured by an enzyme immunoassay (EIA), but the EIA has poor sensitivity with a low positive rate for a relatively small hepatoma. Accordingly, an electrochemiluminescence immunoassay (ECLIA) utilizing an antigen or an antibody which is labeled with an Ru complex was recently developed for a further highly sensitive measurement. The application of the electrochemiluminescence immunoassay led successfully to higher sensitivity in the PIVKA-II measurement. To realize higher sensitivity not only in the ECLIA, but also in an enzyme immunoassay, a chemiluminescence assay, a radio-isotope assay, latex turbidimetry or the like, the influence of an unspecific reaction in a sample should be taken into consideration.

In the process of studies for eliminating the influence of the unspecific reaction in a sample in the PIVKA-II measurement, it has been found that sensitivity and specificity of the measurement could be improved by adding to the reagents, thrombin and/or an antibody that reacts with a sensitivity with human fibrin-like related substances. As the substances attributable to such an unspecific reaction in the sample, attention was directed first to fibrin or its related substances in the sample, and second to thrombin bound to fibrin or its related substances. In particular, when a polyclonal antibody is used as an anti-human prothrombin antibody for a second antibody or a labeled antibody, it may be subject to the interference of these unspecific reaction substances, thereby causing positive errors in measurement of PIVKA-II. It is reported that the protein structure of prothrombin is composed of an $F_1$ fragment, an $F_2$ fragment and thrombin. The labeled antibody used for measurement of PIVKA-II may be not only an anti-prothrombin antibody, but also an anti-$F_1$ antibody, an anti-$F_2$ antibody, or an anti-$(F_1+F_2)$ antibody. However, in consideration of the purity of these antibodies or the similarity of thrombin to the antigen, these antibodies may also react with bound or free thrombin in a sample. Further, in measurement of PIVKA-II, fibrin or its insoluble related substances in a sample are physically adsorbed onto carriers such as magnetic beads, glass beads, latexes, plastic plates or the like to give rise to the phenomenon of positive errors in the measurement.

To prevent the interference attributable to fibrin-like related substances and thrombin, antibodies reacting with the human fibrin-like related substances, for example, anti-fibrinogen or anti-fibrin antibodies, and/or thrombin are added to the reagents. Thus, the present invention succeeds in accurately measuring a very small amount of PIVKA-II by effectively inhibiting the nonspecific reaction.

An object of the present invention is to provide an immunoassay utilizing an antigen-antibody reaction for specifically measuring with a high sensitivity PIVKA-II in serum or plasma by adding to reagents thrombin and/or an antibody reacting with human fibrin-like related substances to the reagents.

DISCLOSURE OF THE INVENTION

To solve the problems described above, an immunoassay for measuring PIVKA-II according to the present invention comprises the steps of adding thrombin and/or an antibody reacting with human fibrin-like related substances to the reagents, and measuring PIVKA-II in serum or plasma.

The thrombin described above is preferably a thrombin-containing animal serum and/or purified thrombin, which may be heated or unheated.

In the present invention, the antibodies reacting with human fibrin-like related substances include, by way of example, anti-fibrinogen antibodies, anti-fibrin antibodies or the like, which are preferably polyclonal antibodies, especially those highly reactive with not only fibrinogen or fibrin, but also fibrin-like related substances, such as FDP, fibrinopeptide A or fibrinopeptide B. As for the thrombin, purified preparations are derived from human beings or animals, such as cows, pigs, sheep, horses, rabbits and chickens. Further, the use of a wide variety of thrombin-containing animal serums, such as bovine serum, sheep serum, porcine serum, horse serum, chicken serum and rabbit serum derived from animals different from the species of animals immunized for obtaining the labeled antibodies or second antibodies may lead to reaction inhibition of anti-thrombin antibodies occurring as impurities in the labeled antibodies.

As the labeled antibodies or second antibodies used in the present invention, it is possible to use not only human polyclonal antibodies against prothrombin, $F_1$, $F_2$, or $F_1+F_2$, but also human monoclonal antibodies against prothrombin, $F_1$, $F_2$, or $F_1+F_2$. Here, $F_1$ and $F_2$ are peptides constituting prothrombin. Polyclonal or monoclonal antibodies prepared by immunization with synthetic peptides having the antigenicity of prothrombin can also be used.

The Examples of the present specification show application to an electrochemiluminescence immunoassay. The present invention is also useful in a chemiluminescence assay, a radioisotope assay or the like to achieve a higher sensitivity. In the present invention, antibodies such as anti-fibrinogen antibody and anti-fibrin antibody reacting with fibrin-like related substances such as fibrinogen, fibrin, FDP, fibrinopeptide A and fibrinopeptide B are preferably obtained by immunization with human-derived fibrin-like related substances, but antibodies obtained by immunization with fibrin-like related substances such as animal-derived fibrinogen, fibrin or the like, and cross-reacting with human-derived fibrin-like related substances can also be used. Antibodies, such as anti-fibrinogen or anti-fibrin antibodies specific to fibrin-like related substances, are preferably added to a reaction solution in the first reaction of the 2-step sandwich method. On the other hand, thrombin is preferably added to the labeled antibody solution or the second antibody solution in the second reaction, the amount added thereof being preferably 1 to 50 NIH/ml. Those antibodies specific to fibrin-like related substances, such as anti-fibrinogen or anti-fibrin antibodies, a purified thrombin, and an animal serum containing thrombin may be used singly or jointly as the occasion demands.

The animal serums containing thrombin, such as bovine serum, sheep serum, porcine serum, horse serum, chicken serum and rabbit serum are derived from animals different from the species of animals immunized for obtaining the labeled antibodies or second antibodies, and may be preferably added in an amount of 1 to 20%. These animal serums are derived from different species of animals and may be blended, when necessary, with animal serums derived from the same species of animals immunized for obtaining the labeled antibody or second antibody.

If the enzyme activity of thrombin is strong when adding thrombin to reagents, the immune reaction may be adversely affected. If animal serums are added to those reagents containing the labeled antibodies or second antibodies, the stability of the reagents may be adversely affected. Therefore, a protease inhibitor for inhibiting the enzyme activity of thrombin is preferably added to the reagents to which thrombin or animal serums are added.

As the protease inhibitor, it is possible to use inhibitors, mentioned on page 452 in "Rinsho Koso Handbook (Clinical Enzyme Handbook)" (1st ed., edited by Kitamura, Baba et al. and issued by Kodansha Scientific Co., on Sep. 10, 1982), such as, plasma proteinous inhibitors, hirudine, benzamidine and synthetic inhibitor such as PMSF (phenylmethylsulfonyl fluoride), NPGB and or the like. However, these inhibitors are not sufficient for inhibiting the enzyme activity of thrombin, so it has been found that the enzyme activity is significantly reduced without losing its antigenicity even when a purified preparation of thrombin is subjected to heat treatment, e.g., at about 40 to 65° C.

A commercial purified preparation of thrombin is to be stored primarily in a refrigerated or frozen form and not to be exposed to a high temperature; The heating temperature for thrombin used in the present invention is 30 to 70° C., particularly preferably 40 to 60° C., so that the heating time can be reduced to 15 to 60 minutes. As a matter of course, this heating is aimed at inactivating the enzyme activity of thrombin, and hence insofar as the enzyme can be inactivated without losing its antigenicity, the heating temperature and heating time are not limited to the above ranges.

If the animal serum derived from animals of species different from animals immunized for the labeled antibody is previously heated for use as thrombin, the heating temperature is preferably 50 to 65° C. and the heating time is preferably 15 to 60 minutes. However, the heating time and heating temperature, needless to say, can be regulated without particular limitation in case of need. Further, the animal serum can be used without heating, if necessary.

BEST MODE FOR CARRYING OUT THE INVENTION

Hereinafter, the present invention is described by reference to the Examples, but these Examples are shown for illustrative purposes only and are not construed as restrictive.

EXAMPLE 1

An Example of Measurement by an Electrochemiluminescence Immunoassay in an Automatic Analyzer Picolumi 8220

After 50 μl of a sample was added to 150 μl of a reaction solution, 25 μl of magnetic beads having anti-PIVKA-II monoclonal antibody immobilized thereon were added thereto. After they were reacted at 30° C. for 9 minutes, 350 μl of a Picolumi BF washing solution (10 mM Tris buffer) was added, and the magnetic beads trapped by a magnet were washed 3 times. Then, 200 μl of Ru-labeled antibody solution containing 1 μg/ml of a Ru-labeled anti-human prothrombin antibody (derived from rabbit) was added to the magnetic beads, and these were allowed to react at 30° C. for 9 minutes. Likewise, the magnetic beads trapped by a magnet were washed 3 times with the Picolumi BF washing solution. After addition of 300 μl of a Picolumi luminescent electrolytic solution containing 0.1 M tripropyl amine, the magnetic beads were sent to the surface of an electrode and the luminescence of Ru bound to the magnetic beads was measured, the amount of PIVKA-II in the sample being determined.

Reagent Composition

Reaction solution: 50 mM Tris buffer (pH 7.8), 0.150 M NaCl, 0.01% Tween 20, 0.1% $NaN_3$, 5% rabbit serum (heated).

Ru-labeled antibody solution: 50 mM Tris buffer (pH 7.8), 0.150 M NaCl, 0.01% Tween 20, 0.1% $NaN_3$, 1 mM PMSF, 1 μg/ml Ru-labeled anti-human prothrombin antibody (derived from rabbit), 5% rabbit serum (heated).

(Preparation of Solid-Phase Magnetic Beads Having Anti-PIVKA-II Monoclonal Antibody)

1 ml of 30 mg/ml magnetic beads (4.5 microns) was placed into a test tube and trapped with a magnet. After the supernatant was discarded, 1 ml of 0.5 mg/ml anti-PIVKA-II monoclonal antibody (in 150 mM phosphate buffer, pH 7.8) was added to the magnetic beads, and these were allowed to react at room temperature for 1 day under stirring. After the magnetic beads were washed, 2 ml of 1% BSA-Phosphate buffer was added thereto, and the magnetic beads were blocked for 1 day under stirring at room temperature. In case of use, the magnetic beads were diluted to 1 mg/ml with the 1% BSA-Phosphate buffer.

(Preparation of Ru-Labeled Anti-Human Prothrombin Antibody)

68 μl of Ru-complex compound of ruthenium-tridipyridyl modified with a succinimide group was added to 1 ml of 1 mg/ml anti-human prothrombin antibody immunized with rabbits, and these were allowed to react for 30 minutes under stirring at room temperature. Then, the reaction was terminated by adding 50 μl of 2 M glycine, and further the sample was allowed to react for 10 minutes under stirring at room temperature. Finally, the sample was applied onto Sephadex G-25 (previously equilibrated with 10 mM phosphate buffer), and fractions of Ru-bound protein were collected. The Ru-labeled anti-human prothrombin antibody thus obtained was diluted to 1 μg/ml in case of use.

180 μg/ml of anti-human fibrinogen antibody (derived from rabbit) was added to each reaction solution, a control solution without the anti-human fibrinogen antibody (derived from rabbit) and 8 human serums being used to compare their specificity. Each serum was measured at n=3, and the results are shown in Table 1. Those reagents with the anti-human fibrinogen antibody (derived from rabbit) show low dispersion in measured values and the absence of unspecific reaction.

TABLE 1

| | Control | | C.V. | Addition of anti-fibrinogen antibody (180 μg/ml) | | | C.V. |
|---|---|---|---|---|---|---|---|
| 1 | 56 | 38 | 98 | 50.0% | 26 | 23 | 24 | 6.3% |
| 2 | 47 | 45 | 35 | 15.2% | 27 | 27 | 28 | 2.1% |
| 3 | 37 | 35 | 30 | 10.6% | 26 | 33 | 29 | 12.0% |
| 4 | 55 | 21 | 25 | 55.2% | 20 | 22 | 19 | 7.5% |
| 5 | 27 | 37 | 44 | 23.7% | 15 | 19 | 15 | 14.1% |
| 6 | 21 | 23 | 26 | 10.8% | 19 | 19 | 20 | 3.0% |
| 7 | 22 | 31 | 22 | 20.8% | 21 | 20 | 18 | 7.8% |
| 8 | 30 | 24 | 24 | 13.3% | 24 | 24 | 24 | 0.0% | mAU/ml

EXAMPLE 2

In this example, the same reagent composition in Example 1 was used except that 10 NIH/ml of a purified preparation of bovine thrombin or human thrombin was added to the Ru-labeled antibody solution. This sample showing particularly highly unspecific reactions was selected and measured simultaneously for PIVKA-II at n=10. The results of this sample and a control sample in which neither the bovine thrombin nor the human thrombin was added are shown in Table 2.

When the purified preparation of bovine or human thrombin was added to the reagent, the specificity of the sample was improved as compared with the control sample. This sample serum was centrifuged at 3000 rpm for 10 minutes and an obtained supernatant thereof showed 80 mAU/ml.

EXAMPLE 3

In this example, the same reagent composition in Example 1 was used except that 180 μg/ml anti-human fibrinogen antibody (derived from rabbit) was added to the reaction solution and 10 NIH/ml bovine thrombin was added to the Ru-labeled antibody solution. This sample, which showed a highly unspecific reaction, was measured simultaneously for PIVKA-11 at n=10. The results of this sample and a control sample to which neither the anti-human fibrinogen antibody (derived from rabbit) nor the bovine thrombin was added are shown in Table 2 with the results in Example 2. Addition of both the anti-human fibrinogen antibody (derived from rabbit) and bovine thrombin leads to an increase in specificity of PIVKA-II much more in comparison with addition of bovine thrombin alone.

TABLE 2 mAU/ml

| | Control | Addition of human thrombin | Addition of bovine thrombin | Use of both bovine thrombin and anti-human fibrinogen antibody |
|---|---|---|---|---|
| 1 | 365 | 121 | 99 | 97 |
| 2 | 219 | 83 | 145 | 80 |
| 3 | 158 | 83 | 112 | 79 |
| 4 | 209 | 88 | 107 | 89 |
| 5 | 202 | 95 | 119 | 72 |
| 6 | 150 | 154 | 104 | 79 |
| 7 | 247 | 84 | 110 | 80 |
| 8 | 133 | 110 | 103 | 82 |
| 9 | 166 | 121 | 94 | 85 |
| 10 | 245 | 92 | 103 | 100 |
| Mean | 209.4 | 103.1 | 109.6 | 84.3 |

EXAMPLE 4

500 NIH of a purified preparation of bovine thrombin was added to 1 ml of 50 mM Tris buffer (0.15 M NaCl, pH 7.8) and heated at 50° C. for 30 minutes in a thermostatic water bath. In this example, the same reagent composition in Example 1 was used except that 180 μg/ml anti-human fibrinogen antibody (derived from rabbit) was added to the reaction solution and the heat-treated purified preparation of bovine thrombin was added at a concentration of 5 NIH/ml to the Ru-labeled antibody solution. Using this sample, which showed a high unspecific reaction, PIVKA-II was measured. The results of this sample and a control sample to which neither the anti-human fibrinogen antibody (derived from rabbit) nor the heated bovine thrombin was added are shown in Table 3. As is evident from the results in Table 3, the inhibitory effect of the sample solutions in this example against the unspecific reaction was exhibited similarly in Example 3. The enzyme activity of this heated thrombin, as measured using Chromozyme TH (Boehringer), was reduced to ⅕ compared with that of the unheated thrombin.

TABLE 3 mAU/ml

| | Control | Use of both heated bovine thrombin and anti-human fibrinogen antibody |
|---|---|---|
| 1 | 133 | 105 |
| 2 | 154 | 87 |
| 3 | 152 | 92 |
| 4 | 219 | 132 |
| 5 | 150 | 52 |
| 6 | 100 | 87 |
| 7 | 137 | 98 |
| 8 | 125 | 90 |
| 9 | 162 | 89 |
| 10 | 127 | 86 |
| Mean | 145.9 | 91.8 |

EXAMPLES 5 And 6

In this example, the same reagent composition in Example 1 was used except that 5% unheated rabbit serum (a control where the final concentration of the rabbit serum was 10%), 5% unheated horse serum (Example 5), or 5% unheated sheep serum (Example 6) was added to Ru-labeled antibody solution, respectively. This sample, which showed a highly unspecific reaction was measured for its inhibitory effect against the unspecific reaction, and the results are shown in Table 4.

TABLE 4 mAU/ml

| | Control | Rabbit serum + horse serum | Rabbit serum + sheep serum |
|---|---|---|---|
| 1 | 208 | 114 | 114 |
| 2 | 190 | 104 | 109 |
| 3 | 196 | 107 | 120 |
| 4 | 179 | 135 | 136 |
| 5 | 242 | 170 | 132 |
| Mean | 203 | 126 | 122 |

As compared with the control, the unspecific reaction was inhibited in the sample to which the horse serum or sheep serum was added. This sample, which showed a highly unspecific reaction was centrifuged at 3000 rpm for 10 minutes, and a supernatant was obtained which showed 74 mAU/ml.

Capability of Exploitation in Industry:

As described above, according to the present invention, PIVKA-II in serum or plasma can be measured specifically with high sensitivity by adding thrombin and/or an antibody reacting with human fibrin-like related substances to the reagents.

What is claimed is:

1. An immunoassay method for measuring PIVKA-II in a serum or plasma test sample, comprising the steps of:
   (a) contacting the serum or plasma test sample with a first immunoassay reagent comprising anti-PIVKA-II antibodies and antibodies which specifically bind to a human fibrin or a human fibrinogen;
   (b) contacting the resultant sample with a second immunoassay reagent comprising labeled antibodies which bind PIVKA-II, wherein the labeled antibodies are at least one antibody selected from the group consisting of anti-human prothrombin antibody, anti-$F_1$ antibody to the $F_1$ prothrombin fragment, anti-$F_2$ antibody to the $F_2$ prothrombin fragment and anti-($F_1$+$F_2$) antibody to the $F_1$ and $F_2$ prothrombin fragments; and
   (c) measuring the labeled antibodies, thereby measuring PIVKA-II in the serum or plasma test sample.

2. The immunoassay method according to claim 1, wherein the second immunoassay reagent further comprises thrombin.

3. The immunoassay method according to claim 2, wherein the thrombin is a thrombin-containing animal serum and/or a purified thrombin.

* * * * *